(12) United States Patent
Kalmbach et al.

(10) Patent No.: US 10,835,571 B2
(45) Date of Patent: Nov. 17, 2020

(54) METHOD OF INCREASING OMEGA-3 CONTENT IN POULTRY

(71) Applicant: Kalmbach Feeds, Inc., Upper Sandusky, OH (US)

(72) Inventors: Paul M. Kalmbach, Upper Sandusky, OH (US); Simon M. Shane, Upper Sandusky, OH (US)

(73) Assignee: KALMBACH FEEDS, INC., Upper Sandusky, OH (US)

( * ) Notice: Subject to any disclaimer, the term of this patent is extended or adjusted under 35 U.S.C. 154(b) by 166 days.

(21) Appl. No.: 15/914,542

(22) Filed: Mar. 7, 2018

(65) Prior Publication Data

US 2018/0193402 A1    Jul. 12, 2018

Related U.S. Application Data

(62) Division of application No. 13/905,284, filed on May 30, 2013, now abandoned.

(60) Provisional application No. 61/653,678, filed on May 31, 2012.

(51) Int. Cl.
*A61K 36/899* (2006.01)
*A61K 36/55* (2006.01)

(52) U.S. Cl.
CPC ............ *A61K 36/899* (2013.01); *A61K 36/55* (2013.01)

(58) Field of Classification Search
None
See application file for complete search history.

(56) References Cited

U.S. PATENT DOCUMENTS

| 2004/0185148 A1 | 9/2004 | Said |
| 2008/0248154 A1 | 10/2008 | Wiens |
| 2010/0233313 A1 | 9/2010 | Hartnell et al. |

OTHER PUBLICATIONS

Wenk (Asian-Aus. J. Anim. Sci. (2000), vol. 13, No. 1, pp. 86-95).
Wenger Feeds, Enzymes in Poultry Feeds, Dec. 10, 2015, pp. 1-3 US.

*Primary Examiner* — Susan Hoffman
(74) *Attorney, Agent, or Firm* — Standley Law Group LLP; Jeffrey Standley; Beverly Marsh

(57) ABSTRACT

A feed supplement for poultry consisting of distillers dried grains with solubles (DDGS) and flaxseed. The supplement is prepared using a dry extrusion process. Also described is a method of using the feed supplement to increase omega-3 fatty acids in poultry products, such as eggs. Also described is a method of obtaining a poultry egg using the feed supplement.

2 Claims, No Drawings

METHOD OF INCREASING OMEGA-3 CONTENT IN POULTRY

CROSS REFERENCE TO RELATED APPLICATIONS

This application is a divisional of U.S. patent application Ser. No. 13/905,284 filed on May 30, 2013, now abandoned, which claims priority to U.S. Provisional Application No. 61/653,678 filed on May 31, 2012, and is herein incorporated by reference in its entirety.

TECHNICAL FIELD

Exemplary embodiments of the inventive concept relate to feed supplements and methods of increasing the amount of essential fatty acids in eggs and meat of poultry. In particular, the present invention relates to a feed supplement comprised of co-extruded flaxseed and distillers dried grains with solubles (DDGS) that increases the content of omega-3 fatty acids in eggs and meat of poultry.

BACKGROUND OF THE INVENTION

Essential fatty acids (EFAs) are necessary for proper human health. There are two groups of EFAs; the omega-3 fatty acids, and the omega-6 fatty acids. A healthy human diet requires a balance of both omega-3 and omega-6 fatty acids, which play an important role in brain function, metabolism regulation, heart health, bone health, normal growth and development, and reproductive health. However, humans cannot make their own EFAs, and therefore they must be acquired through the foods they eat. Common sources for EFAs have historically included fish oils and plant oils such as flaxseed oil.

There have also been efforts to increase the content of omega-3 in poultry products. This is desirable since a large segment of the population routinely eats poultry products, and many consumers seek to increase the amount of omega-3 in their diet through the foods that they eat. However, there is difficulty in providing a feed product for poultry that results in a high amount of omega-3 content in the poultry products, such as eggs. Many feeds and supplements do not result in poultry products that have omega -3 levels high enough to attract consumers.

SUMMARY OF THE INVENTION

Provided herein is a method for preparing a feed component for poultry, which includes the steps of grinding a quantity of DDGS into a meal, mixing the ground DDGS with intact oilseeds, and co-extruding the mixture. During extrusion, the mixture may reach temperatures of about 220 F to about 320 F. After extrusion, the mixture may be further mixed with additives, which may include enzymes to aid in digestibility and stabilizers. The oilseeds used may be selected from the group consisting of flax, sunflower, safflower, rapeseed, canola, soybean, or combinations thereof.

Also provided herein is a method of increasing the amount of omega-3 in a poultry product which is performed by identifying a bird fed a standard feed ration, and feeding the bird a modified feed ration where 1-15% of the standard feed ration contents are replaced by an extruded mixture of ground DDGS and intact oilseeds. This method may also include the step of obtaining a poultry product from the bird that has an increased omega-3 fatty acid level when compared to the same poultry product obtained from a similar bird fed the standard feed ration. The poultry product may be an egg.

Additional objects, advantages and novel features of the invention will be set forth in part in the description which follows, and in part will be apparent to those skilled in the art upon examination of the following, or may be learned from practice of the invention.

DETAILED DESCRIPTION

Described herein is an improved feed supplement for poultry that is comprised of distillers dried grains and solubles (DDGS) and oilseeds such as flax. As will be appreciated by one of ordinary skill in the art, different types of corn and wheat derivatives may be used in combination with many different types of oilseeds. When fed to poultry over a period of time, higher levels of omega-3 are present in the poultry products, including eggs and meat.

The feed supplement may be prepared by grinding a predetermined amount of DDGS into a meal or flour. The meal or flour is then mixed with flax oilseeds in order to form a homogenous mixture. The oilseeds may be whole or ground. The homogenous mixture is then subjected to a dry extrusion process. During the dry extrusion process, the mixture is subjected to a combination of heat and pressure. The temperature in the extruder may be anywhere from 220-320 degrees while the extrusion process is underway. The pressure may be anywhere from 200 psi to 800 psi. The combination of heat and pressure ruptures the oilseeds, releasing oil into the mixture, and causing the ruptured oilseed to be coated by the ground DDGS. The effect of heat and pressure on the mixture is to not only rupture the oilseeds, but to also gelatinize the starch, and increase the digestibility of the proteins, fats, and fibers in the mixture. As the mixture passes out of the extruder in meal form, heat and pressure are relieved, and the mixture is allowed to cool. Once cooled, additives such as enzymes and stabilizers may be added to aid in consumption by poultry. As will be appreciated by one of ordinary skill in the art, while the mixture may be left in meal form, other suitable feed shapes include feed pellets, feed crumbles, and any other shapes and/or textures that may be desired for feeding poultry.

Preferably, the feed supplement has a minimum crude protein content of 18-28%, and a minimum crude fat content of 16-26%. Preferably, omega-3 fatty acid is 6-12% of the total supplement. Preferably, the feed supplement has a maximum crude fiber content of 12%. Preferably, the supplement also has the following minimum nutritional values: lysine: 0.6-1.2%; methionine: 0.3-0.6%; calcium: 0.05-1.5%; and phosphorus: 0.2-1%. In other embodiments, these nutrient profiles may vary.

In one embodiment, the feed supplement is comprised of 49.625% DDGS, 50% flax, 0.125 dried *aspergillus niger* fermentation product, and 0.25 ethoxyquin. The dried *aspergillus niger* fermentation product is an enzyme to aid in digestibility and the ethoxyquin is a stabilizer to maintain freshness. In other embodiments, the relative amounts of these ingredients may vary significantly. Flax may each comprise anywhere from 10-90% of the supplement; DDGS may also comprise anywhere from 10-90% of the supplement. The dried *aspergillus niger* fermentation product may comprise anywhere from 0-1% of the supplement, and ethoxyquin may also comprise anywhere from 0-1% of the supplement.

In another embodiment, different oilseeds are used instead of flax. The oilseeds may be sunflower, safflower, rapeseed, canola, or soybean. In some embodiments mixtures of different oilseeds may be used.

In some embodiments, different grain or processed grain by-products may be used instead of, or in addition to, DDGS. Grain products that may be used include barley, corn, grain sorghums, mixed feed oats, oats, wheat, rice, rye, triticale, or any mixture thereof. Grain by-products that may be used include aspirated grain fractions, brewers dried grains, buckwheat middlings, condensed distillers soluble, condensed fermented corn extractives, corn bran, corn flour, corn germ meal, corn gluten feed, corn gluten meal, corn grits, distillers dried grains, distillers dried soluble, grain sorghum germ cake, grain sorghum germ meal, grain sorghum grits, grain sorghum mill feed, hominy feed, malt sprouts, oat groats, oat meal, pearl barley by-products, peanut skins, rice bran, rice polishings, rye middlings, sorghum grain flour, wheat bran, wheat flour, wheat shorts, wheat germ meal, wheat middlings, wheat millrun, wheat red dog, or any mixture thereof.

The enzymes and stabilizers used may vary as well, depending on the embodiment. In some embodiments, enzymes and stabilizers may not be added to the supplement, and in other embodiments the supplement may contain either an enzyme or a stabilizer, but not both. In some embodiments, Vitamins A, D, or E may be added to the supplement.

As discussed herein, the supplement may be used to replace anywhere from 1-15% of a standard feeding ration for poultry. However, in some embodiments the supplement may comprise more than 15% of the feed ration for poultry.

As used herein, "poultry" refers to any number of birds that may be kept for purposes of harvesting their eggs, meat, or other poultry products. These include, but are by no means limited to, chickens, turkeys, ducks, geese, quail, and ostrich.

As used herein, "poultry products" refers to any part of a bird that may be used for consumption or other purposes. Poultry products include, but are not limited to, eggs, meat, feet, livers, and hearts. When the poultry product is an "egg", to "obtain" means to collect the egg or eggs from a bird. When the poultry product is meat or another body part of the bird, to "obtain" means to cut out that part of the bird.

As shown in the examples, poultry fed the feed supplement prepared according to the invention experience an increase in omega-3 levels.

The invention is further illustrated by way of the following examples. However, one of ordinary skill in the art will recognize that the invention is in no way limited by the examples.

Example 1: Comparative Analysis of Supplement

In a first example, a feed supplement ("SUPP1") containing the following ingredients is prepared:
50% Flax seeds
49.625% DDGS
0.125% Dried *Aspergillus Niger* Fermentation Product
0.25% Ethoxyquin The flax seeds and DDGS are combined and extruded at a temperature around 260 degrees to create a meal. After the meal has cooled, the dried *aspergillus niger* fermentation product and ethoxyquin are added.

Once prepared, the feed supplement exhibited the nutritional information shown in Table 1 below:

TABLE 1

Nutritional Information of SUPP1

| Nutrient Name | Units | Value |
|---|---|---|
| CR PROTEIN | PCT | 24.000 |
| CRUDE FAT | PCT | 21.500 |
| CRUDE FIBER | PCT | 7.500 |
| CALCIUM | PCT | .500 |
| PHOS-TOTAL | PCT | .670 |
| PHOS-AVAIL | PCT | 1.000 |
| M E POULTRY | KCL/LB | 1,870.000 |
| LYSINE | PCT | 1.000 |
| EQIV LYSINE | PCT | 1.000 |
| METHIONINE | PCT | .500 |
| METH & CYSTINE | PCT | 1.000 |
| TRYPTHOPHAN | PCT | .290 |
| ARGININE | PCT | 1.610 |
| THREONINE | PCT | .950 |
| LINOLEIC ACID | % | 3.000 |
| DRY MATTER | PCT | 92.000 |
| XANTHOPHYLL | MG/LB | 8.014 |
| SALT | PCT | .350 |
| ASH | PCT | 6.354 |
| VIT A (TOTAL) | KIU/LB | 1.550 |
| VITAMIN D-3 | KIC/LB | .175 |
| RIBOFLAVIN | MG/LB | 4.306 |
| CHOLINE | MG/LB | 968.397 |
| NIACIN | MG/LB | 41.184 |
| PANTOTHENTIC ACI | MG/LB | 8.095 |
| VITAMIN B-12 | MCG/LB | 6.564 |
| FOLIC ACID | MG/LB | .454 |
| BIOTIN | MG/LB | .349 |
| THIAMIN | MG/LB | 4.316 |
| PYRIDOXINE | MG/LB | 3.252 |
| VITAMIN E | IU/LB | 11.000 |
| SODIUM | PCT | .220 |
| POTASSIUM | PCT | .911 |
| MAGNESIUM | PCT | .291 |
| SULFUR | PCT | .473 |
| SELENIUM | PPM | .153 |
| CHLORIDE | PCT | .229 |
| MANGANESE | MG/LB | 23.178 |
| ZINC | MG/LB | 38.076 |
| IRON | MG/LB | 52.489 |
| COPPER | MG/LB | 3.950 |
| COBALT | MG/LB | .117 |

Three different groups of chickens were obtained and fed three different dietary treatments. One of the treatments, T1, did not include the feed supplement, while the other two treatments, T3 and T4, contained the supplement as 6% and 10% of the total dietary treatment, respectively. The ingredients of the dietary treatments T1, T3 and T4 is shown in Table 2 below:

TABLE 2

Dietary Treatment Rations (as-fed basis)

| Ingredient, lb | T1 (No Supp1) | T3 (6% Supp1) | T4 (10% Supp1) |
|---|---|---|---|
| Corn | 1150 | 965 | 895 |
| Soybean Meal | 370 | 290 | 280 |
| DDGs | 200 | 200 | 200 |
| Wheat Midds | 55 | 200 | 200 |
| Canola Oil | — | 10 | 10 |
| Calcium Carbonate (Small) | 116 | 119 | 119 |
| Calcium Carbonate (Large) | 75 | 75 | 75 |
| SUPP1 | — | 120 | 200 |
| Salt | 5.3 | 4.8 | 4.6 |
| Sodium Carbonate | 2.0 | 2.0 | 2.0 |
| Monocalcium Phosphate | 13.0 | — | — |
| Lysine | 0.85 | 1.85 | 1.55 |
| DL Methionine | 2.25 | 2.35 | 2.20 |

TABLE 2-continued

Dietary Treatment Rations (as-fed basis)

| Ingredient, lb | T1 (No Supp1) | T3 (6% Supp1) | T4 (10% Supp1) |
|---|---|---|---|
| Vitamin/Trace Mineral Premix | 10 | 10 | 10 |
| Choline Chloride | 0.50 | 0.50 | 0.50 |
| Allzyme SSF | 0.30 | 0.30 | 0.30 |
| Ronozyme P-CT | 0.22 | 0.22 | 0.22 |
| Total | 2,000.42 | 2,001.02 | 1,999.37 |

A table of comparative nutritional value of the different dietary treatments is shown in Table 3 below.

TABLE 3

Nutritional Value of Dietary Treatments

| Nutrients | T1 (No Supp1) | T3 (6% Supp1) | T4 (10% Supp1) |
|---|---|---|---|
| ME Poultry, kcal/lb | 1300 | 1300 | 1308 |
| Crude Protein, % | 16.5 | 16.5 | 17.0 |
| Crude Fat, % | 3.6 | 5.2 | 5.9 |
| Crude Fiber, % | 2.8 | 3.6 | 3.8 |
| Calcium, % | 4.0 | 4.1 | 4.1 |
| Phosphorus, % | 0.69 | 0.70 | 0.71 |
| Total Lysine, % | 0.89 | 0.88 | 0.88 |
| Total Methionine, % | 0.43 | 0.43 | 0.43 |
| Total Met + Cys, % | .73 | .74 | .75 |
| Sodium, % | 0.18 | 0.19 | 0.19 |

The chickens used were Lohmann Selected Leghorn (LSL) laying hens that were in lay upon allotment to treatments. The hens were fed the T1 control diet for four weeks prior to the start of the trial. Once the trial began, the laying hens were fed only one of the T1, T3 or T4 dietary treatments for the duration of the trial.

A randomized complete block design was used, where the blocking factor was room location and cage level. 18 cages containing two compartments each were used, and each compartment contained 2-3 hens, for a total of 96 hens. Each compartment contained a bowl waterer and a self-feeder. The room contained a light timer/dimmer system that provided the hens with 16 hours of artificial daylight. Forced air ventilation was used in the room, and the room temperature was set at 68° F.

Nine replications per treatment were used, and the trial was six weeks in length. Individual eggs were collected and weighed daily to determine the size category of each egg. The number of eggs per compartment was recorded daily by size category, which was done pursuant to American Egg Board classifications, which can be found at www.aeb.org. In order to perform nutrient profiling of the eggs, two eggs from each pen were collected on Day 0 (prior to the start of the trial), Day 14, Day 18, and Day 42. After each collection period, collected eggs were sent to Lipid Technologies, Austin, Minnesota, for analysis. The two eggs from each pen were pooled together for nutritional analysis. The Omega-3 content of the eggs of the laying hens fed the four different dietary treatments are shown in Table 4 below. These parameters are based on mg/50 g pooled egg sample (no shell).

TABLE 4

Comparison of Omega-3 content in Eggs of Laying Hens

| Parameter | T1 | T3 | T4 |
|---|---|---|---|
| Total Omega 3 FA, mg | | | |
| D14 | 49.4 | 125.7 | 208.3 |
| D28 | 59.2 | 150.6 | 210.1 |
| D42 | 46.7 | 148.2 | 229.4 |
| Average D14 & D28 | 54.3 | 138.1 | 209.2 |
| Overall Average | 51.8 | 141.5 | 215.9 |

As shown in Table 4, eggs laid by the hens that were fed the T4 dietary treatment that was comprised of 10% SUPP1, had the greatest concentration of Omega-3 fatty acids.

Example 2: Supplement Analyzed Against Specialty Egg Standard Diet

In this Example, the same type of hens and procedures were used as in Example 1, with the following differences: 100 total hens were used, the eggs were collected on Days 21, 28, 35, 49, and 63, and the collected eggs were sent to a specialty egg laboratory for assay.

The ingredients for the dietary treatments used are shown below in Table 5, and designated as T1, T5, T6, and T7. T1 in this example is the same as T1 in the first example. Supp1 is the same as Supp1 in the first example.

TABLE 5

Dietary Treatment Rations (as-fed basis)

| Ingredient, lb | T1 (No Supp1) | T5 (No Supp1) | T6 (3% Supp1) | T7 (6% Supp1) |
|---|---|---|---|---|
| Corn | 1150 | 1095 | 1040 | 965 |
| Soybean Meal | 370 | 345 | 325 | 290 |
| DDGs | 200 | 200 | 200 | 200 |
| Wheat Midds | 55 | 110 | 150 | 200 |
| Canola Oil | — | 10 | 10 | 10 |
| Calcium Carbonate (Small) | 116 | 114 | 119 | 119 |
| Calcium Carbonate (Large) | 75 | 75 | 75 | 75 |
| SUPP1 | — | — | 60 | 120 |
| Flaxseed | — | 30 | — | — |
| Salt | 5.3 | 4.6 | 5.3 | 4.8 |
| Sodium Carbonate | 2.0 | 2.0 | 2.0 | 2.0 |
| Monocalcium Phosphate | 13.0 | 2.0 | 1.0 | — |
| Lysine | 0.85 | 1.05 | 1.35 | 1.85 |
| DL Methionine | 2.25 | 2.35 | 2.35 | 2.35 |
| Vitamin/Trace Mineral Premix | 10 | 10 | 10 | 10 |
| Choline Chloride | 0.50 | 0.50 | 0.50 | 0.50 |
| Allzyme SSF | 0.30 | 0.30 | 0.30 | 0.30 |
| Ronozyme P-CT | 0.22 | 0.22 | 0.22 | 0.22 |
| Total | 2,000.42 | 2,002.02 | 2,002.02 | 2,001.02 |

T5 is an specialty egg standard diet, with one difference between it and the T1 dietary treatment is that it contains flaxseed.

A table of comparative nutritional value of the different dietary treatments is shown in Table 6 below.

TABLE 6

Nutritional Value of Dietary Treatments

| Nutrients | T1 (No Supp1) | T5 (No Supp1) | T6 (3% Supp1) | T7 (6% Supp1) |
|---|---|---|---|---|
| ME Poultry, kcal/lb | 1300 | 1300 | 1300 | 1308 |
| Crude Protein, % | 16.5 | 16.5 | 16.5 | 16.5 |
| Crude Fat, % | 3.6 | 4.5 | 4.6 | 5.2 |
| Crude Fiber, % | 2.8 | 3.1 | 3.3 | 3.6 |
| Calcium, % | 4.0 | 4.0 | 4.1 | 4.1 |
| Phosphorus, % | 0.69 | 0.70 | 0.69 | 0.70 |
| Total Lysine, % | 0.89 | 0.89 | 0.89 | 0.88 |
| Total Methionine, % | 0.43 | 0.43 | 0.43 | 0.43 |
| Total Met + Cys, % | .73 | .73 | .73 | .74 |
| Sodium, % | 0.18 | 0.18 | 0.19 | 0.19 |

The baseline omega-3 concentrations of eggs prior to the trial were 63 mg. Table 7, shown below, shows a comparison of the Omega-3 content in the hens fed T1, T5, T6, and T7.

TABLE 7

Comparison of Omega-3 content in Eggs of Laying Hens

| Parameter | T1 | T5 | T6 | T7 |
|---|---|---|---|---|
| Total Omega 3 FA, mg | | | | |
| D21 | 59.38 | 99.26 | 104.26 | 142.44 |
| D28 | 50.78 | 95.56 | 104.11 | 136.44 |
| D49 | 55.89 | 96.11 | 103.72 | 139.44 |
| Average D21 & D28 | 54.39 | 96.61 | 103.72 | 139.44 |
| Overall Average | 54.96 | 96.39 | 101.91 | 137.41 |

After 49 days, all of the hens were placed on the control diet for 28 days. In Table 8 below is shown the resulting levels of Omega-3 in the eggs at day 63, 14 days after all hens were placed on the control diet.

TABLE 8

Omega-3 content in eggs on Day 63

| Parameter | T1 | T5 | T6 | T7 |
|---|---|---|---|---|
| Total Omega 3 FA, mg | | | | |
| D63 | 68.44 | 71.44 | 71.67 | 73.00 |

The results from this trial showed that eggs from hens fed with the T7 dietary treatment (containing 6% Supp1) had the greatest omega-3 fatty acid concentrations when compared to the control diet (T1), and the T5 and T6 diets. The Omega-3 concentrations decreased to normal levels 14 days after the hens were removed from their dietary treatments and placed back on the control diet. The T6 and T7 dietary treatments did not impact egg size, laying rate, or ADFI of the hens during the test period, or the post-test period.

Example 2: Analysis of Amino Acid Digestibility and True Metabolizable Energy (TME)

The amino acid digestibility and true metabolizable energy (TME) of whole flax seed, ground flax seed, DDGS, and co-extruded flaxseed and DDGS (50% flaxseed, 50% DDGS) was tested. First, the amino acid concentrations in flax, DDGS, and extruded flax+DDGS were analyzed. The results are shown in Table 9 below:

TABLE 9

Amino Acid Concentrations (%) in flax, DDGS, and extruded flax + DDGS

| Amino Acid | Flax | DDGS | Theoretical of 50/50% | Extruded Flax + DDGS | % Improvement |
|---|---|---|---|---|---|
| ASP | 2.05 | 1.70 | 1.88 | 2.12 | 12.8 |
| THR | 0.79 | 1.04 | .92 | 1.06 | 15.2 |
| SER | 0.88 | 1.20 | 1.04 | 1.29 | 24.0 |
| GLU | 3.90 | 3.68 | 3.79 | 4.40 | 16.1 |
| PRO | 0.76 | 2.08 | 1.42 | 1.68 | 18.3 |
| GLY | 1.29 | 1.06 | 1.18 | 1.30 | 10.2 |
| ALA | 0.99 | 1.86 | 1.43 | 1.65 | 15.4 |
| CYS | 0.35 | 0.51 | .43 | 0.49 | 14.0 |
| VAL | 1.17 | 1.33 | 1.25 | 1.25 | 0 |
| MET | 0.42 | 0.54 | .48 | 0.53 | 10.4 |
| ILE | 0.99 | 1.05 | 1.02 | 0.98 | −4.0 |
| LEU | 1.32 | 3.04 | 2.18 | 2.52 | 15.6 |
| TYR | 0.56 | 0.99 | .78 | 0.92 | 17.9 |
| PHE | 1.08 | 1.28 | 1.18 | 1.29 | 9.3 |
| LYS | 0.88 | 0.93 | .9 | 0.95 | 5.6 |
| HIS | 0.51 | 0.79 | .65 | 0.71 | 9.2 |
| ARG | 2.12 | 1.22 | 1.67 | 1.81 | 8.4 |
| TRP | 0.27 | 0.21 | .24 | 0.29 | 20.8 |

The lysine content of the combination of flaxseed and DDGS on a dry matter basis is 0.905% compared to 0.950% for the extruded combination. This represents an increase of 4.9% in the extruded combination versus the dry combination. In converting to an "as fed" basis, the lysine content of the combination is 0.83% compared to 0.92% for the co-extruded product, or an uplift of 10.8%.

The methionine content for the combination of flaxseed and DDGS is 0.48% on a dry matter basis compared with 0.53% for the co-extruded product, providing an uplift of 10.4%. The corresponding methionine value expresses "as fed" is 0.46% for the combination and 0.51% for the co-extruded product, providing an uplift of 17.6%.

The dry matter cystine content for the combination is 0.43% and 0.49% for the coextruded product, providing an uplift of 13.9%. The corresponding "as fed" cystine values for the combination are 0.39% and 0.47% for the co-extruded product, contributing to a 20.5% uplift.

The total sulphur-containing amino acid content (methionine and cystine) for the combination on a dry matter basis was 0.91% compared to 1.03% for the extruded product for an uplift of 10.1%. The corresponding value for the combination on an "as fed" basis was 0.826% for the co-extruded product was 0.99% providing an uplift of 19.9%.

The true metabolizable energy of whole flax, ground flax, DDGS, and extruded flax+DDGS was also compared, and the data is shown in Table 10 below.

TABLE 10

True Metabolizable Energy Evaluation of whole flax, ground flax, DDGS, and Extruded Flax + DDGS

| Sample | Gross Energy as-is(kcal/g) | Dry Matter (%) | Avg. $TME_n$ (kcal/g DM) |
|---|---|---|---|
| Whole Flax[1] | 6.287 | 93.5 | 2.783 |
| DDGS | 4.787 | 88.9 | 3.068 |
| Extruded | 5.717 | 96.6 | 3.791 |

TABLE 10-continued

True Metabolizable Energy Evaluation of whole flax, ground flax, DDGS, and Extruded Flax + DDGS

| Sample | Gross Energy as-is(kcal/g) | Dry Matter (%) | Avg. $TME_n$ (kcal/g DM) |
|---|---|---|---|
| Flax + DDGS | | | |

The true metabolizable energy (tME) value of the theoretical mixture of 50% whole flax and DDGS is 2,926 kcal/kg (1,330 kcals/lb). The equivalent value for the co-extruded product is 3,791 kcal/kg (1,723 kcals/lb). This represents a 29.6% improvement in tME. The "as fed" value for the combination of whole flax and DDGS is 2,664 kcal/kg (1,211 kcals/lb) and for the co-extruded product 3,662 kcal/kg (1,664 kcals/kg), representing a 37% uplift on an "as fed" basis.

It is noted that there is a significant (43%) increase in tME when whole flax is ground. Unfortunately, this process releases oil which is subject to rancidity. This in turn potentially affects both production and the flavor of eggs and poultry meat, especially when fed at high levels (up to 5%) in diets While certain embodiments of the present invention are described in detail above, the scope of the invention is not to be considered limited by such disclosure, and modifications are possible without departing from the spirit of the invention as evidenced by the claims. One skilled in the art would recognize that such modifications are possible without departing from the scope of the claimed invention.

The invention claimed is:

1. A method of obtaining a poultry egg, comprising:
   grinding a quantity of DDGS into a DDGS meal;
   selecting a quantity of intact oilseeds containing fatty acids;
   mixing the quantity of intact oilseeds with a quantity of the DDGS meal that is at least equal to the quantity of intact oilseeds, thereby forming a mixture;
   heating the mixture to a temperature between about 220 F to about 320 F;
   extruding the mixture under a pressure between 200 psi and 800 psi;
   cooling the mixture;
   adding an enzyme for aiding digestability to the cooled mixture;
   adding a stabilizer to the cooled mixture;
   feeding the mixture to an egg-laying bird, wherein the mixture is used to replace a portion of a standard feed ration given to the egg-laying bird; and
   obtaining a poultry egg from the bird, wherein the poultry egg has a fatty acid level of at least 200 mg per 50 g egg.

2. The method of claim 1, wherein the fatty acid is omega-3 fatty acid.

* * * * *